US010821430B2

(12) United States Patent
Syed et al.

(10) Patent No.: US 10,821,430 B2
(45) Date of Patent: Nov. 3, 2020

(54) PROCESS FOR PREPARING AN EPOXIDATION CATALYST

(71) Applicant: Dow Technology Investments LLC, Midland, MI (US)

(72) Inventors: Mohmed A. Syed, Lake Jackson, TX (US); Apoorva Kulkarni, Pearland, TX (US); Vera P. Santos Castro, Terneuzen (NL); Victor J. Sussman, Midland, MI (US); John C. McKeen, Hope, MI (US); Cathy L. Tway, Midland, MI (US); Clifford S. Todd, Midland, MI (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 16/328,033

(22) PCT Filed: Aug. 30, 2017

(86) PCT No.: PCT/US2017/049287
§ 371 (c)(1),
(2) Date: Feb. 25, 2019

(87) PCT Pub. No.: WO2018/044982
PCT Pub. Date: Mar. 8, 2018

(65) Prior Publication Data
US 2019/0184387 A1  Jun. 20, 2019

Related U.S. Application Data

(60) Provisional application No. 62/382,800, filed on Sep. 2, 2016.

(51) Int. Cl.
| | |
|---|---|
| *B01J 37/02* | (2006.01) |
| *B01J 23/50* | (2006.01) |
| *B01J 37/00* | (2006.01) |
| *C07C 213/04* | (2006.01) |
| *C07D 301/10* | (2006.01) |
| *C07D 317/36* | (2006.01) |
| *C07C 215/08* | (2006.01) |
| *C07D 317/04* | (2006.01) |
| *B01J 21/04* | (2006.01) |
| *B01J 35/10* | (2006.01) |
| *B01J 37/08* | (2006.01) |
| *C07C 29/00* | (2006.01) |
| *C07C 41/02* | (2006.01) |
| *C07C 68/00* | (2020.01) |
| *C07C 213/00* | (2006.01) |
| *C07D 301/03* | (2006.01) |

(52) U.S. Cl.
CPC .......... *B01J 37/0205* (2013.01); *B01J 21/04* (2013.01); *B01J 23/50* (2013.01); *B01J 35/1009* (2013.01); *B01J 35/109* (2013.01); *B01J 35/1042* (2013.01); *B01J 35/1076* (2013.01); *B01J 35/1095* (2013.01); *B01J 37/009* (2013.01); *B01J 37/08* (2013.01); *C07C 29/00* (2013.01); *C07C 41/02* (2013.01); *C07C 68/00* (2013.01); *C07C 213/00* (2013.01); *C07C 213/04* (2013.01); *C07C 215/08* (2013.01); *C07D 301/03* (2013.01); *C07D 301/10* (2013.01); *C07D 317/04* (2013.01); *C07D 317/36* (2013.01)

(58) Field of Classification Search
CPC ........ B01J 21/04; B01J 23/50; B01J 35/1009; B01J 35/1042; B01J 35/1076; B01J 35/109; B01J 35/1095; B01J 37/009; B01J 37/08; C07C 29/00; C07C 41/02; C07C 68/00; C07C 213/00; C07C 213/04; C07C 215/08; C07D 301/03; C07D 301/10; C07D 317/04; C07D 317/36
USPC ....................................................... 502/348
See application file for complete search history.

(56) References Cited

U.S. PATENT DOCUMENTS

| | | | |
|---|---|---|---|
| 4,242,235 A | 12/1980 | Cognion et al. | |
| 5,100,859 A * | 3/1992 | Gerdes | B01J 23/02 502/439 |
| 5,187,140 A | 2/1993 | Thorsteinson et al. | |
| 7,977,274 B2 | 7/2011 | Gueckel | |

(Continued)

FOREIGN PATENT DOCUMENTS

WO     WO-2019133174 A1 *  7/2019  ............. B01J 23/50

OTHER PUBLICATIONS

Thai; Vietnam Journal of Chemistry, International Edition, 2017, 55, 595-601. (Year: 2017).*

(Continued)

*Primary Examiner* — Daniel R Carcanague

(57) ABSTRACT

A process for preparing a silver-containing catalyst for the selective oxidation of ethylene to ethylene oxide including the steps of: (a) providing a multimodal support, (b) preparing an impregnation solution comprising a silver component, (c) impregnating, at least once, the multimodal support of step (a) with the silver-containing impregnation solution of step (b) to form an impregnated support; (d) subjecting the impregnated multimodal support from step (c) to a removal means, such as a centrifuge, at least once, for a time sufficient to remove impregnated silver impregnation solution from the multimodal support and to control the amount of silver in the pores of the multimodal support by selectively removing impregnated silver impregnation solution from a set of larger pores in the multimodal support; (e) roasting, at least once, the multimodal support after the step (d); (f) optionally, repeating the impregnation step (c), (g) optionally, repeating the centrifugation step (d), and (h) optionally, repeating the calcination step (e).

12 Claims, 8 Drawing Sheets

(56) References Cited

U.S. PATENT DOCUMENTS

| | | | | |
|---|---|---|---|---|
| 2006/0258532 | A1* | 11/2006 | Thorsteinson | B01J 21/04 502/347 |
| 2006/0281631 | A1* | 12/2006 | Gerdes | B01J 21/04 502/263 |
| 2008/0015393 | A1* | 1/2008 | Matusz | B01J 23/50 568/497 |
| 2008/0125610 | A1* | 5/2008 | Lockemeyer | B01J 23/50 564/503 |
| 2009/0131695 | A1* | 5/2009 | Gerdes | B01J 23/50 549/534 |
| 2009/0198076 | A1* | 8/2009 | Guckel | B01J 23/688 549/536 |
| 2010/0191006 | A1* | 7/2010 | Guckel | B01J 27/187 549/536 |
| 2012/0264952 | A1* | 10/2012 | Rosendahl | C07D 301/10 549/534 |
| 2012/0323026 | A1* | 12/2012 | Lockemeyer | B01J 35/108 549/536 |
| 2014/0100379 | A1 | 4/2014 | Richard et al. | |

OTHER PUBLICATIONS

Goncharova, S. N., Paukshtis, E. A., & Bal'Zhinimaev, B. S. (1995). Size effects in ethylene oxidation on silver catalysts. Influence of support and Cs promoter. Applied Catalysis A: General, 126(1), 67-84.

PCT/US2017/049287, International Preliminary Report on Patentability dated Mar. 5, 2019.

PCT/US2017/049287, International Search Report and Written Opinion dated Nov. 20, 2017.

* cited by examiner

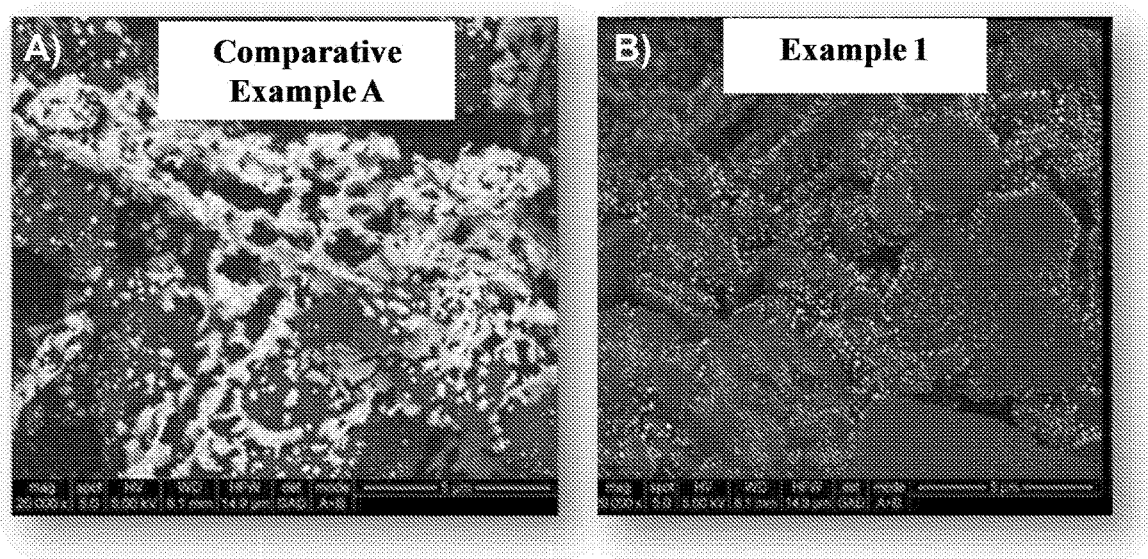
Fig. 5a    Fig. 5b
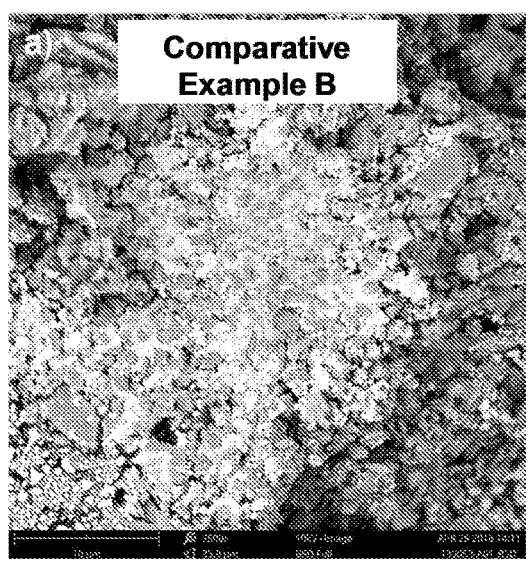 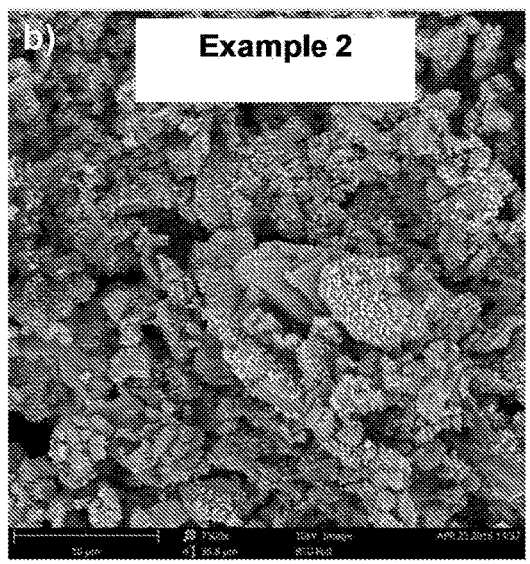
Fig. 6a    Fig. 6b

PROCESS FOR PREPARING AN EPOXIDATION CATALYST

FIELD

The present invention is related to a process for preparing an epoxidation catalyst. More specifically, the present invention is related to a process for preparing a silver-containing catalyst useful for olefin epoxidations.

BACKGROUND

The production of ethylene oxide via a catalytic epoxidation of ethylene in the presence of oxygen and in the presence of a silver-based catalyst is known. In general, the epoxidation reaction includes the step of contacting a feed containing at least ethylene and oxygen with a supported silver-containing catalyst resulting in the production of the corresponding ethylene oxide (EO). Commercial catalysts used for producing EO are known to include silver (Ag) particles supported on an alumina support.

While previous efforts have sought to improve the selectivity (synonymous to efficiency), activity and stability of olefin epoxidation catalysts by employing multimodal supports, none of the prior art discloses a way to control Ag particle size in each type of pores in a multimodal support. Extensive research has demonstrated that the particle size of Ag affects significantly the catalyst activity and selectivity. FIG. 1 is reproduced from the work developed by Goncharova et al., in "Size effects in ethylene oxidation on silver catalysts. Influence of support and Cs promoter." Applied Catalysis A: General, 126(1), 67-84; and FIG. 1 demonstrates the effect of particle size on selectivity for several catalysts, including Ag supported on $\alpha$-$Al_2O_3$, $SiO_2$ and bulk Ag. Goncharova et al. demonstrated that within the range studied, the selectivity is found to increase with particle size (20-100 nm) for the supported catalysts. Furthermore, the Ag bulk shows lower selectivity than Ag supported on $\alpha$-$Al_2O_3$, demonstrating that large aggregates are less efficient in the epoxidation reaction.

Current state of the art does not allow the control of the Ag particle size as a function of pore size, particularly for supports with multi-modal pore size distributions. For example, large agglomerates can easily form on large pores of multimodal supports using known processes for making a catalyst; and as a result, less than optimal performance of the catalyst is achieved using such multimodal supports with large agglomerates.

SUMMARY

One embodiment of the present invention is directed to a process for preparing a silver-containing catalyst for the oxidation of ethylene to ethylene oxide (EO) including the steps of:

(a) providing a porous multimodal support having at least a first set of support pores of a first size range and at least a second set of support pores of a second size range wherein the second size range of the second set of support pores is smaller than the first size range of the first set of support pores;

(b) providing an impregnation solution, such as an impregnation solution comprising a silver component, for impregnating the impregnation solution into the at least first set of support pores and the at least second set of support pores of the porous multimodal support;

(c) impregnating, at least one time (i.e., at least once), the porous multimodal support with a least a portion of the impregnation solution from step (b);

(d) selectively removing the impregnation solution prior to fixing the silver upon the carrier at least the first set of support pores of the porous multimodal catalyst support by subjecting, at least once, the impregnated porous multimodal support after the impregnation step (c) to a removal means for a time sufficient to selectively remove at least a portion of impregnated silver impregnation solution contained in the at least first set of support pores of the porous multimodal catalyst support.

In another embodiment, the process for preparing a silver-containing catalyst may include the additional step of:

(e) roasting (i.e. calcining), at least once, the impregnated catalyst support member from step (d) for a time and temperature sufficient to form a silver-containing catalyst useful for the epoxidation of olefins.

In still another embodiment, the selective removal means in step (d) may include a centrifuge for centrifuging the impregnated catalyst support member to remove at least a portion of impregnated solution contained in the at least first set of support pores.

In an optional embodiment, the impregnation step (c) or the removing step (d) may be repeated, at least one more time, for a time sufficient to remove further the Ag impregnation solution contained in the catalyst support member.

In further embodiment, the removing step (d) may be carried out at least two times before the roasting step (e). The centrifugation step (d) is advantageously performed at a centrifugal force and for a period of time sufficient to remove the Ag solution from the desired pores and to provide the support with a more evenly distributed Ag particle size in the multimodal pores of the catalyst support after roasting.

In even yet other embodiments, any one or more of the above steps (a)-(e) can optionally be repeated any number of times as desired and sufficiently to control the amount of Ag deposited in the pores of the catalyst support.

Also provided in the present application is a reaction system for producing ethylene oxide from a feed comprising ethylene and oxygen over an ethylene oxide catalyst prepared by the process of the present invention.

BRIEF DESCRIPTION OF THE DRAWINGS

The drawings show non-limiting embodiments of the present invention wherein:

FIG. 5a is a scanning electron micrograph (SEM) fracture cross section image of Ag particles in the larger pore diameter pore mode of a multimodal EO catalyst support, where the Ag impregnation is performed by a conventional method and does not include a centrifugation step. Unless otherwise noted, pores smaller than 5 microns are considered herein as "small" pores; and pores greater than 5 microns are considered here as "large" pores.

FIG. 5b is a SEM fracture cross section image of Ag particles in the larger diameter pore mode of a multimodal EO catalyst support, where the Ag impregnated samples are subjected to a centrifugation step after the Ag solution is impregnated in the support, as described in FIG. 2.

FIG. 6a is a SEM fracture cross section image of Ag particles in the larger diameter pore mode of a multimodal EO catalyst support, where the Ag impregnation is performed by a single impregnation step (conventional synthesis without a centrifugation step).

FIG. 6b is a SEM fracture cross section image of Ag particles found in the larger diameter pore mode of a multimodal EO catalyst support, where Ag is impregnated in a single step followed by a centrifugation step, as described in FIG. 2.

DETAILED DESCRIPTION

Figure 1:
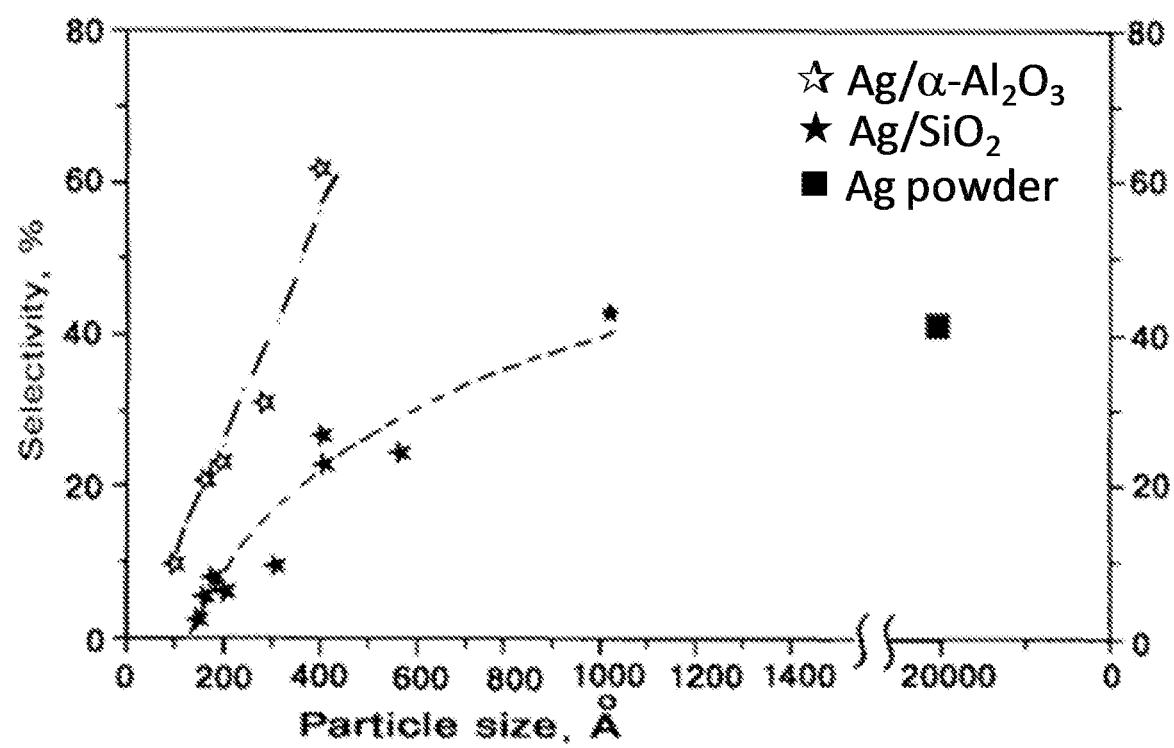
FIG. 1 is graphical illustration of the effect of Ag particle size on ethylene oxide selectivity taken from Goncharova et al., in "Size effects in ethylene oxidation on silver catalysts. Influence of support and Cs promoter." Applied Catalysis A: General, 126(1), 67-84. The symbols illustrated in FIG. 1 represent the following: Ag/$\alpha$-$Al_2O_3$ (☆); Ag/$SiO_2$ (★) and Ag powder (■). The epoxidation conditions of the process includes the following: 230° C., 1 bar, 2% CAL, 7% $O_2$ in $N_2$.

"Catalyst" herein means a substance that increases the rate of a chemical reaction.

In an epoxidation reaction, ethylene reacts with oxygen or an oxygen-containing gas in the presence of a supported Ag catalyst in a reactor to form ethylene oxide. The epoxidation reaction can be characterized in terms of "activity", "selectivity" and/or "productivity" of the epoxidation reaction.

For example, the "selectivity" of an epoxidation reaction, which is synonymous with "efficiency," refers to the relative amount (as a fraction or in percent) of converted or reacted ethylene that forms the corresponding ethylene oxide product. The terms "efficiency" and "selectivity" are used interchangeably herein. For example, the "efficiency to ethylene oxide" refers to the percentage on a molar basis of converted or reacted ethylene that forms ethylene oxide. The "yield" of ethylene oxide refers to the net number of moles of ethylene oxide produced by the process divided by the net number of moles of ethylene fed to the process for any given time period.

The "activity" of a catalyst, for example in a fixed bed reactor, is generally defined as the reaction rate towards the desired product per unit of catalyst volume in the reactor. The activity relates to both the total number of available active sites on the catalyst and the reaction rate of each site.

In addition, the "activity" of an epoxidation reaction can be quantified in a number of ways, one being the mole percent of ethylene oxide contained in an outlet stream of a reactor relative to that in an inlet stream of the reactor (the mole percent of olefin oxide in the inlet stream typically, but not necessarily, approaches zero percent) while the reactor temperature is maintained substantially constant; and another being the temperature required to maintain a given rate of ethylene oxide production. In some instances, activity is measured over a period of time in terms of the mole percent of ethylene oxide produced at a specified constant temperature. Alternatively, the "activity" of an epoxidation reaction can be measured as a function of the temperature required to sustain production of ethylene oxide at a specified rate, given other conditions such as pressure and total moles in the feed.

"Promoters," sometimes referred to as "inhibitors" or "moderators," refer to materials that enhance the performance of the catalysts by either increasing the rate towards the desired formation of ethylene oxide and/or suppressing the undesirable oxidation of ethylene or ethylene oxide to carbon dioxide and water, relative to the desired formation of ethylene oxide.

The terms "reaction temperature," "epoxidation temperature" or "epoxidation reaction temperature" refer to any selected temperature(s) that are directly or indirectly indicative of the catalyst bed temperature of a reactor. In certain embodiments, the reaction temperature may be a catalyst bed temperature at a specific location in the catalyst bed. In other embodiments, the reaction temperature may be a numerical average of several catalyst bed temperature measurements made along one or more catalyst bed dimensions (e.g., along the length). In additional embodiments, the reaction temperature may be the reactor outlet gas temperature. In further embodiments, the reaction temperature may be the reactor inlet or outlet coolant temperature.

As used herein, the term "reaction product" includes both unreacted feed components and those components that are generated as a result of a chemical reaction. In an ethylene oxide production process, for example, the "reaction product" includes ethylene oxide product; and if present, any by-products (such as carbon dioxide) and/or unreacted feed components (such as ethylene, oxygen, and/or chlorides).

"Silver loading" herein means weight percent or weight fraction of the catalyst that is silver and based on the calcined catalyst. Silver loading can be determined by X-ray fluorescence, titration or other means known to those skilled in the art (Neutron activation analysis, NAA).

"Silver particle size" herein refers to average particle size in nanometers as measured by dynamic pulse CO chemisorption method, scanning electron microscopy (SEM) or other means known to those skilled in the art.

Dynamic pulse CO chemisorption method enables the determination of exposed silver sites and is based on the reaction of CO on an oxidized Ag surface, producing $CO_2$. The average particle size diameter from the CO titration experiments can be determined by the following expression:

$$d = \frac{\sigma_{Ag}}{N_A} \frac{6}{\rho_{Ag}} \frac{n_{Ag}}{n_{CO_2}}$$

wherein $\sigma_{Ag}$ is the average atomic surface density of silver, $\rho_{Ag}$ is the density of silver, $N_A$ is the Avogadro's number, $n_{Ag}$ is the mol of Ag present on the sample and 11032 is the total mol of $CO_2$ produced. The stoichiometry between the surface atoms and adsorbed gas is considered to be equal to 1.

A "multimodal pore size distribution", with reference to a catalyst support, herein means a support wherein the pore size is a continuous probability distribution with at least two different modes determined by methods (such as Hg porosimetry) known by those skilled in the art.

A "bimodal pore size distribution", with reference to a catalyst support, herein means a continuous probability distribution of pore size of pores with two different modes.

The terms "control" or "controlling", with reference to a particle size, herein means primarily using silver concentration in the impregnation solution in conjunction with impregnation, calcination, and a selective removal means to provide silver particles of a desired particle size.

In its broadest scope, the present invention includes a novel process for synthesizing a silver-based catalyst including controlling the Ag particle size in a support containing a multimodal pore size distribution. The silver-based catalyst of the present invention is useful for the epoxidation of ethylene to form ethylene oxide.

The broad general procedure of the present invention for preparing the silver-based catalyst includes at least the following steps: preparing an impregnation solution comprising Ag-containing component(s) useful for impregnating a multimodal support member, contacting and impregnating the multimodal support member with the prepared impregnation solution, and then selectively removing at least a portion of the impregnated impregnation solution from at least one set of pores of the multimodal support.

Figure 2:
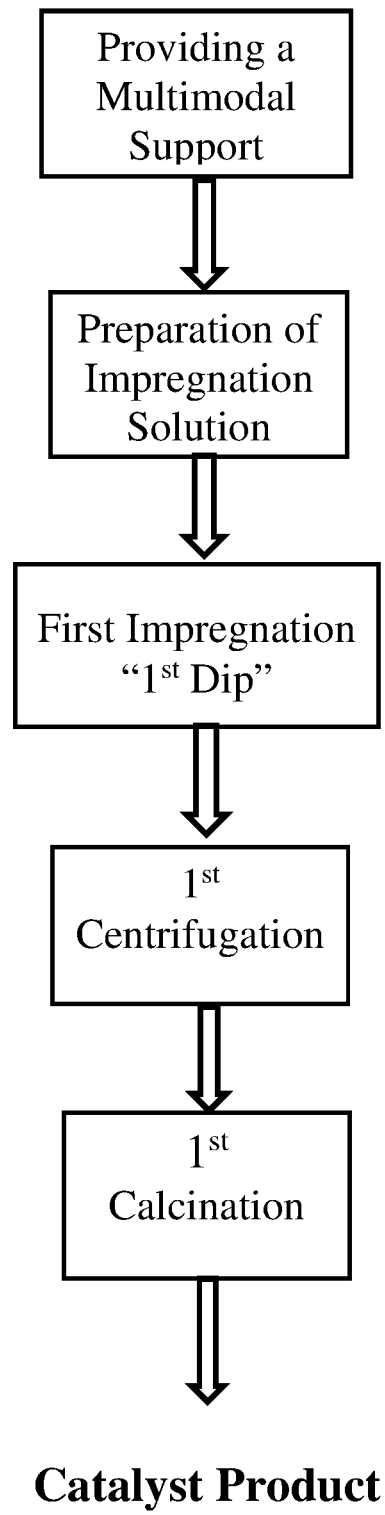
FIG. 2 is a schematic flow diagram showing a synthesis of a catalyst according to the process of the present invention.

In one preferred embodiment, the process of the present invention can include for example a five-step process, as schematically illustrated in the schematic flow chart of FIG. 2, including the steps of:

(a) providing a porous multimodal catalyst support member, (b) providing an impregnation solution comprising a Ag component, (c) impregnating the porous catalyst support member with at least a portion of the impregnation solution;

(d) selectively removing Ag component solution from at least one set of pores of the multimodal porous catalyst support member by subjecting the impregnated porous catalyst support member after the impregnation step (c) to a removal means, such as centrifugation, for a time and under conditions sufficient to remove at least a portion of the impregnated silver impregnation solution from at least one set of pores of the porous catalyst support member; and (e) roasting (i.e. calcining) the porous catalyst support member from after step (d) to convert the Ag component to Ag metal and deposit Ag on the interior and exterior surfaces of the porous catalyst support member to form a catalyst; and to provide a uniform distribution of Ag particles having a uniform average particle size.

In other embodiments, the process of the present invention may include one impregnation step or a sequence of two or more impregnation steps. The impregnated support from the impregnation step can then be treated by or subjected to a removal means such as a centrifugation step, followed by a calcination step. Any of the impregnating, centrifuging, or roasting steps of the present invention process may be carried out once (as shown in FIG. 2), or if desired, and in some embodiments, any or all of the steps may be carried out two or more times (as shown in FIGS. 3-4).

Figure 3:
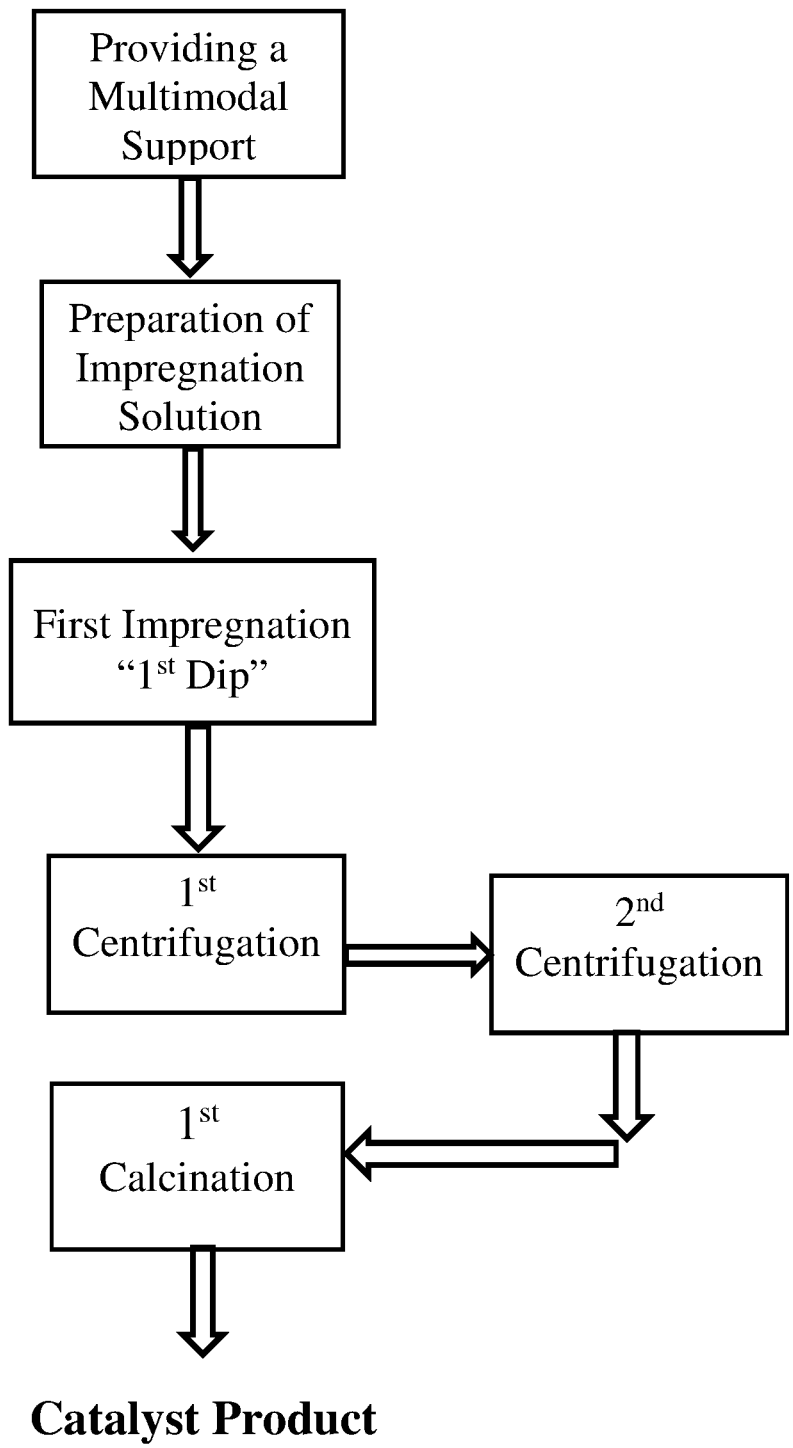
FIG. 3 is another schematic flow diagram showing a synthesis of a catalyst according to the process of the present invention providing for two centrifugation steps.

With reference to FIG. 3, there is shown another embodiment of the process of the present invention wherein a catalyst is impregnated with Ag component solution in a single step and then the impregnated catalyst is subjected to a two centrifugation steps, i.e., a first centrifugation step and sequentially followed by a second centrifugation step.

Figure 4:
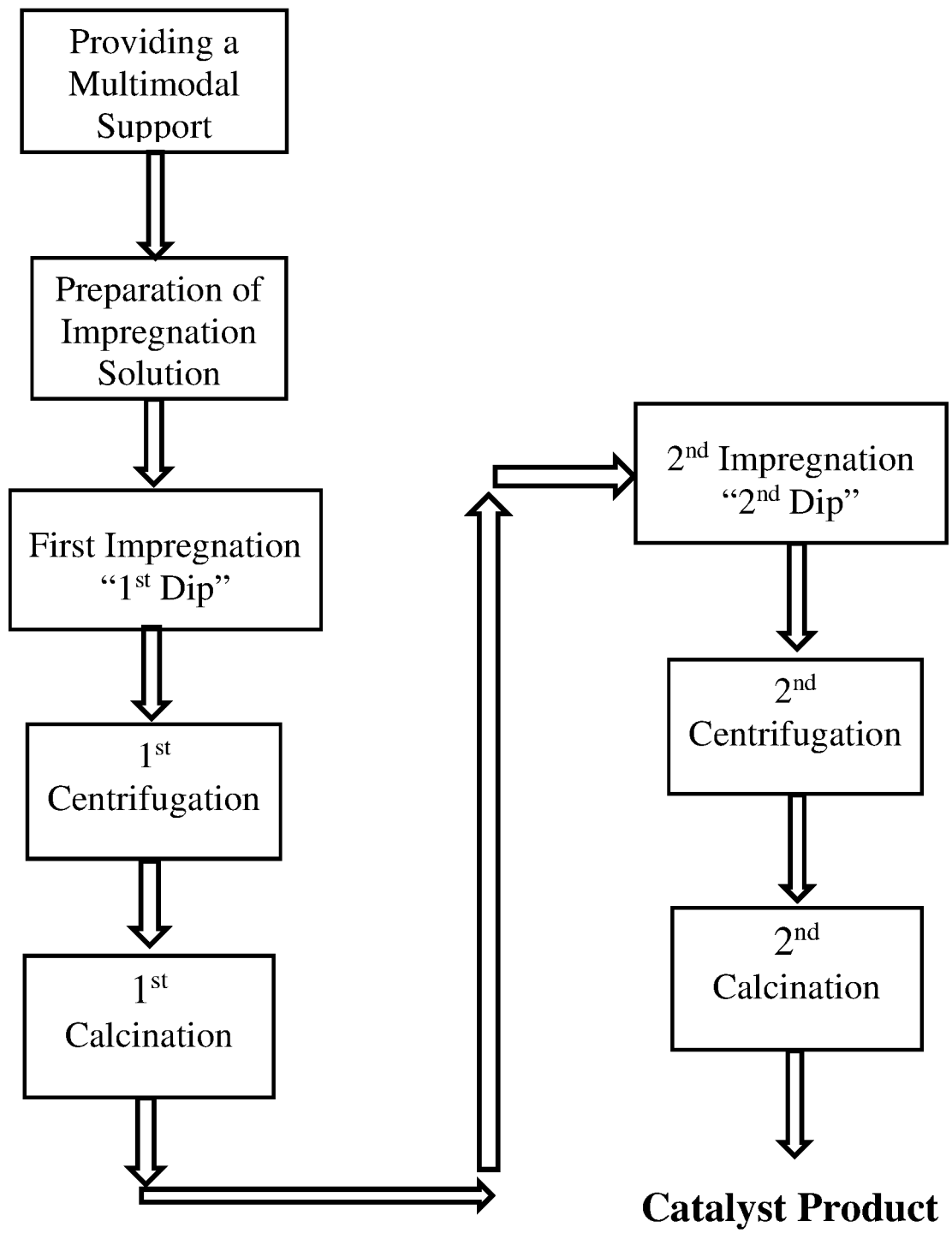
FIG. 4 is another schematic flow diagram showing a synthesis of a catalyst according to the process of the present invention providing for a series of one impregnation step, one centrifugation step, and one calcination step followed in sequence by a second series of a second impregnation step, a second centrifugation step, and a second calcination step.

In another embodiment shown in FIG. 4, the process of the present invention wherein after preparing the silver impregnation solution, the catalyst is subjected to a sequence of a first impregnation step, a first centrifugation step, and a first calcination step in series followed by a sequence of a second impregnation step, a second centrifugation step, and a second calcination step in series. As a result of the process shown in FIG. 4, the catalyst essentially undergoes the series of impregnation, centrifugation and calcination steps twice to produce a catalyst product.

In still another embodiment (not shown), the process of the present invention for preparing a silver-containing catalyst for the epoxidation of olefins can include the steps of: (a) providing a porous multimodal support having at least two modes of pore size distributions; (b) providing a silver-containing impregnation solution for impregnating the impregnation solution into the pores of the porous multimodal support; (c) impregnating the porous multimodal support with the impregnation solution from step (b) to provide the porous multimodal support with a first amount of impregnation solution; (d) centrifuging the impregnated silver-containing impregnation solution from the porous multimodal support to provide the porous multimodal support with a second amount of impregnation solution remaining in the support pores; (e) roasting the impregnated porous multimodal support from step (d); (f) impregnating the porous multimodal support with the impregnation solution from step (b) to provide the porous multimodal support with a third amount of impregnation solution; (g) centrifuging the impregnated silver-containing impregnation solution from the porous multimodal support from step (f) to provide the porous multimodal support with a fourth amount of impregnation solution remaining in the support pores; and (h) roasting the impregnated porous multimodal support from step (g) for a time and temperature sufficient to form a silver-containing catalyst useful for the epoxidation of olefins; and wherein the centrifugation steps (d) and (g) are carried out under different centrifugation conditions.

In yet another embodiment, not shown, the impregnated centrifuged catalyst can be subjected to two calcination steps in sequence, i.e., a first calcination step followed sequentially by a second calcination step at the same or different temperature to provide a catalyst product.

In any of the above embodiments, the removal means may be employed to remove at least 20 percent (%), at least 30%, at least 50% or at least 80% of the impregnated silver-containing impregnation solution contained in the at least first set of support pores of the porous multimodal support. In still another embodiment, up to 100% of the impregnated silver-containing impregnation solution contained in the at least first set of support pores of the porous multimodal support can be removed.

While the above embodiments illustrate variations in the present invention process, the process is not to be limited to those processes shown in the FIGS. 2-4. As aforementioned, the impregnating, centrifuging, or roasting steps may be carried out once, twice or more times; and optionally, any or all of the steps may be carried out two or more times. Any combinations and variations of the steps shown in FIGS. 2-4 will become apparent to those skilled in the art which are within the scope of the present invention process as set forth in the claims herein.

The process for preparing a catalyst in accordance with the present invention starts with a first step of providing a multimodal support (also known as a "support") that is to be impregnated with an impregnation solution. The catalyst preparation process described herein can be applied to different types of supports having a multimodal pore size distribution such as a bimodal support and to other catalysts prepared via impregnation techniques. A multimodal support includes a support having at least two different pore sizes. In general, the porous multimodal support of the present invention may have at least a first set of support pores of a first size range and at least a second set of support pores of a second size range wherein the second size range of the second set of support pores is smaller than the first size range of the first set of support pores.

For example, the first set of support pores may have a second pore size in the range of from about 3 μm to about 100 μm in one embodiment and from about 5 μm to about 50 μm in another embodiment.

For example, the second set of support pores may have a first pore size in the range of from about 0.01 μm to about 3 μm in one embodiment and from about 0.01 μm to about 1 μm in another embodiment.

The supports may comprise any of the known porous refractory structure or support materials, so long as whatever the porous refractory material chosen is relatively inert in the presence of the chemicals and processing conditions employed in the application in which the supports will be utilized.

The support may be selected from a wide range of inert support materials including for example, natural or artificial inorganic support materials such as silicon carbide, clays, pumice, zeolites, charcoal and alkaline earth metal carbonates, such as calcium carbonate and mixtures thereof. Other embodiments may include refractory support materials, such as alumina, magnesia, zirconia and silica; and mixtures thereof. In one preferred embodiment, the support material can be alpha-alumina. In one exemplary embodiment, Ag is deposited on the alpha alumina catalyst support and optionally one or more promoters can be deposited on the catalyst as well.

The materials used for the support may be used with or without a binder. The binder, when used, can be for example an inorganic type of material.

Generally, the multimodal support is provided by preparing the support by well known methods. For example, several well-known methods of preparing supports suitable for use in alkene oxide catalysts are described in WO 2013/148417 A1; and U.S. Pat. Nos. 4,379,134; 4,806,518; 5,063,195; 5,384,302; and 6,831,037 incorporated herein by reference.

For example, an alpha-alumina support of at least 95% purity can be prepared by compounding (mixing) the raw materials, extrusion, drying and a high temperature calcination. In this case, the starting raw materials usually include one or more alpha-alumina powder(s) with different properties, a clay-type material which may be added as binder to provide physical strength, and a burnout material (usually an organic compound) used in the mix to provide desired porosity and/or pore size distribution after its removal during the calcination step. The levels of impurities in the finished support are determined by the purity of the raw materials used, and their degree of volatilization during the calcination step. Common impurities may include silica, alkali and alkaline earth metal oxides and trace amounts of metal and/or non-metal-containing additives.

The alumina can be of a very high purity grade, that is, at least 98 percent by weight or weight percent (wt %) alpha-alumina, any remaining components being silica, alkali metal oxides (for example, sodium oxide) and trace amounts of other metal-containing and/or non-metal-containing additives or impurities. Likewise, the alumina can be of a lower purity, that is, 80 wt % alpha-alumina, the balance being one or more of amorphous and/or crystalline alumina and other alumina oxides, silica, silica alumina, mullite, various alkali metal oxides (for example, potassium oxide and cesium oxide), alkaline earth metal oxides, transition metal oxides (for example, iron oxide and titanium oxide), and other metal and non-metal oxides. In addition, the material used to make the support may comprise components which have been known for improving catalyst performance, for example, rhenium, (such as rhenates) and molybdenum.

The alpha-alumina support may have a pore volume of at least 0.3 cubic centimeters per gram ($cm^3/g$) in one embodiment, and from about 0.4 $cm^3/g$ to about 2.0 $cm^3/g$ in another embodiment; pore diameters may range from about 0.1 micron to about 50 microns.

The alpha-alumina support may have a specific surface area of at least about 0.5 square meters per gram ($m^2/g$) in one embodiment, and at least about 0.7 $m^2/g$ in another embodiment. The surface area of the alpha-alumina support may be less than about 10 $m^2/g$ in one embodiment, and less than about 5 $m^2/g$ in another embodiment.

The alpha-alumina support useful in the present invention can be of any suitable shape. Exemplary shapes of the support includes pills, chunks, tablets, pieces, pellets, rings, spheres, wagon wheels, toroids having star shaped inner and/or outer surfaces, and the like.

The support can be of any size suitable for employment in reactors. For example, in a fixed bed ethylene oxide reactor having a plurality of parallel elongated tubes (in a suitable shell) 1 inch to 3 inches (2.5 cm to 7.5 cm) outer diameter and 15 feet to 45 feet (4.5 m to 13.5 m) long filled with catalyst, it is desirable to employ alpha alumina support having a rounded shape, such as, for example, spheres, pellets, rings, cross-partitioned rings, penta-rings, tablets, and the like, having diameters from 0.1 inch (0.25 cm) to 0.8 inch (2 cm).

The impregnation solution useful in the present invention includes a silver-containing impregnation solution. While in one embodiment, a bimetallic system can be used which may include silver and another metal such as copper or gold, typically silver alone is impregnated into a support. The silver impregnation solution used to impregnate the support comprises a silver component in an impregnating medium such as solvent or complexing/solubilizing agent as disclosed in U.S. Pat. No. 5,187,140 incorporated herein by reference.

The particular silver component employed in the present invention may be chosen, for example, from among silver complexes, nitrate, silver oxide or silver carboxylates, such as silver acetate, oxalate, citrate, phthalate, lactate, propionate, butyrate and higher fatty acid salts; and mixtures thereof. In another embodiment, silver oxide complexed with amines may be the form of silver that may be used in the practice of the present invention.

A wide variety of solvents or complexing/solubilizing agents may be employed to solubilize the above silver component to the desired concentration in the impregnating medium or solution. The solvent can be any conventional solvent or any complexing/solubilizing agent known in the art so long as the solvents or complexing/solubilizing agents can solubilize the silver component to the desired concentration in the impregnating solution, and the solvent or the complexing/solubilizing agent does not detrimentally affect the performance properties of the catalyst. Among the solvents or complexing/solubilizing agents suitable for this purpose may include for example lactic acid (as disclosed in U.S. Pat. Nos. 2,477,436 and 3,501,417); ammonia (as disclosed U.S. Pat. No. 2,463,228); alcohols, such as ethylene glycol (as disclosed in U.S. Pat. Nos. 2,825,701 and 3,563,914); and amines and aqueous mixtures of amines (as disclosed in U.S. Pat. Nos. 2,459,896; 3,563,914; 3,215,750; 3,702,259; 4,097,414; 4,374,260; and 4,321,206) all of which are incorporated herein by reference. A combination of two or more of the above solvents or complexing/solubilizing agents may also be used in the impregnation solution of the present invention.

Generally, the support is impregnated with an impregnation solution that contains an amount of silver, which is an amount of silver capable of catalyzing the direct oxidation of the alkene with oxygen or an oxygen-containing gas to the corresponding alkene oxide. In making such a catalyst, the support may be typically impregnated (one or more times) with one or more silver component solutions sufficient to allow the desired silver to be supported on the support.

Generally, the amount of silver component that is dissolved in the silver impregnation solution is more than that ultimately provided on the finished catalysts per impregnation. For example, $Ag_2O$ can be dissolved in a solution of oxalic acid and ethylenediamine to an extent of approximately [~]30 wt %. Vacuum impregnation of such a solution onto an alpha alumina support of ~0.7 cc/g porosity results in a catalyst containing ~25 wt % of silver based on the entire weight of the catalyst. Accordingly, in order to obtain catalysts having a silver loading of greater than about 25 wt %, greater than about 30 wt %, or more, it is necessary to subject the support to at least two or more sequential impregnations of silver, with or without promoters, until the desired amount of silver is deposited on the support. Two or more impregnations may be used to make the catalysts of the present invention to achieve the desired concentration of silver in the resultant catalyst.

As it is known, the number of impregnations, the concentration of solution used for each impregnation and the calcination conditions are factors that can be used to fine tune the particle size of silver in the resultant catalyst. For example, the concentration of the silver salt can be higher in the latter impregnation solutions than in the first. In other instances, approximately equal concentrations of silver can be used during each impregnation step. In further instances, a greater concentration of silver can be used in the initial impregnation than in subsequent impregnations. Each of the impregnations may be followed by roasting or other procedure to render the silver insoluble. A further advantage of the present invention over the prior art is that the present invention process provides a more selective means of controlling the Ag concentration in selected pores.

Various optional compounds or additives can be added to the impregnation solution including for example one or more promoters, alkali metals, alkali earth metals, and oxyanions, and mixtures thereof. In one embodiment, promoters can be materials that are introduced to catalysts during the preparation of the catalysts (e.g., solid phase promoters, also referred to as "catalyst promoters" herein). In another alternative embodiment, promoters can be gaseous materials that are introduced to the epoxidation reactor feed (gas phase promoters). In one example, an organic halide gas phase promoter may be added continuously to an epoxidation reactor feed to increase the catalyst efficiency. For silver-based ethylene epoxidation catalysts, both solid and gas phase promoters are typically used in a process.

Suitable alkali metal promoter components can be used in forming the impregnation solution if desired. For example, the alkali metal promoter components may include all those promoters that are soluble in the particular solvent or solubilizing agent employed and that are compatible with the other components in the impregnation solution. Accordingly, inorganic and organic components of alkali metals, such as, nitrates, halides, hydroxides, sulfates and carboxylates may be used. As an illustration, alkaline earth salts such as salts of barium, calcium and magnesium can readily be solubilized in the impregnating solution and deposited upon the support in accordance with the process of the present invention.

The sequence of impregnating or depositing the surfaces of the support with silver and promoters is optional. Thus, impregnation and deposition of silver and salts may be effected coincidentally or sequentially, i.e., the promoters may be deposited prior to, during, or subsequent to silver addition to the support. The promoters may be deposited together or sequentially. For example, one or more of the salts may be deposited first followed by the coincidental or sequential deposition of silver and additional or other salts.

Impregnation of the catalyst support may be effected using one or more solutions containing silver and promoters in accordance with well-known procedures for coincidental or sequential depositions. For coincidental deposition, following impregnation the impregnated support is heat or chemically treated to reduce the silver component to silver metal and deposit the salts onto the catalyst surfaces.

For sequential deposition, the support is initially impregnated with silver or promoter (depending upon the sequence employed) and then heat or chemically treated as described above. This is followed by a second impregnation step and a corresponding heat or chemical treatment to produce the finished catalyst containing silver and promoters.

In one embodiment of the present invention, the one or more promoters are added coincidentally with the silver. In another embodiment, the one or more promoters are added to the catalyst in the very last silver impregnation step.

All the components of the impregnation solution are typically mixed and dispersed in a vessel at a temperature enabling the preparation of an effective impregnation solution. For example, the temperature during the mixing of the above components may be generally from about ambient temperature (23° C.) to about 70° C. in one embodiment, and from about ambient temperature to about 50° C. in another embodiment.

The preparation of the impregnation solution of the present invention, and/or any of the steps thereof, may be a batch or a continuous process. The process and type of equipment used to prepare the impregnation solution may be any conventional process or equipment known in the art. For example, a mixing vessel is used to blend or mix the above components: the Ag component, the solvent and optionally any other desirable additives such as promoter(s).

In general, a procedure for depositing silver catalytic material and any other additives such as promoters includes: impregnating a porous alumina support according to the present invention with a solution comprising a solvent or solubilizing agent, silver complex and one or more promoters, if desired. Impregnation of the support is generally the preferred technique for silver deposition, because it utilizes silver more efficiently than coating procedures, the latter being generally unable to effect substantial silver deposition onto the interior surfaces of the support. In addition, coated catalysts are more susceptible to silver loss by mechanical abrasion.

The process and type of equipment used to impregnate the impregnation solution into the support may be any conventional impregnation process or equipment known in the art. For example, a vessel is used to contain the support, which is to be impregnated with the impregnation solution described above, and the impregnation solution is passed through the support in the vessel.

"Surface area," as used herein, refers to the surface area of the supports as determined by the BET (Brunauer, Emmett and Teller) method by nitrogen as described in the Journal of the American Chemical Society 60 (1938) pp. 309-316 incorporated herein by reference. "Total pore volume" means pore volume of the support and is typically determined by mercury porosimetry. The measurements reported herein used the method described in Webb & Orr, Analytical Methods in Fine Particle Technology (1997), p. 155, incorporated herein by reference, using mercury intrusion to 60,000 psia using Micromeritics Autopore IV 9520, incorporated herein by reference, assuming 130° contact angle, 0.485 N/M surface tension of Hg. "Porosity" is the proportion of the non-solid volume to the total volume of material. Total pore volume as measured by mercury porosimetry or water absorption may be used to estimate open porosity by those of skill in the art. Although not of catalytic importance, closed pores will not be determined using these techniques. Put another way, porosity is defined as the void volume (unoccupied space) divided by the total volume of the sample. "Median pore diameter" means the pore diameter corresponding to the point in the pore size distribution at which half of the total pore volume of the support has cumulatively been measured. For multimodal supports, an overall median pore diameter is not fully descriptive of the pore system and median pore diameters for each pore mode are presented instead.

There is an important relationship between silver loading and silver particle size for a given support material. For example, multiple impregnation steps can be used to increase Ag loading. Silver specific surface area is defined as the area of silver divided by the weight of catalyst. It is preferred that procedures for determining the silver specific area be carried out on an un-promoted catalyst. Particular techniques for determining the silver specific area include oxygen and carbon monoxide chemisorptions, and microscopy coupled with image analysis. One particular technique employs selective chemisorption of oxygen using a dynamic pulse technique. Asterios Gavrilidis, et al., Influence of Loading on Metal Surface Area for Silver/Alpha-Alumina Catalysts, J. *Catalysis,* 139(1) at 41-47 (1993) incorporated herein by reference. Another technique uses a titration method to determine the number of silver surface atoms, and by extension, the specific silver surface area. M. Boudart, Turnover Rates in Heterogeneous Catalysis, *Chem. Rev.,* Vol. 95 at 661-666 (1995) incorporated herein by reference.

After the porous catalyst support is impregnated with the impregnation solution (also referred to herein as the "impregnated support"), any impregnation solution that is not impregnated into the pores of the support is referred to herein as "non-impregnated solution". This may include solution around and on the exterior surfaces of the support. The solution that has been impregnated or absorbed into the pores of a catalyst support is referred to herein as the "impregnated solution". It is a feature of this invention that the majority of the non-impregnated solution, if present, and at least a portion of the impregnated solution are removed from the impregnated support in distinct steps.

For example, following each impregnation of the catalyst support with silver-containing impregnation solution, it is desirable that remaining, extra, or excess non-impregnated solution be separated from the overall impregnated support by employing a conventional separation means such as filtering, draining or centrifuging. For example, the non-impregnated solution can be drained away from the impregnated support, i.e., the non-impregnated solution is physically separated from the external surface of the overall support. As another example, when centrifugation is used as the separation means, the centrifugation is used under operating conditions to separate non-impregnated solution from the external surface of the overall impregnated catalyst. Generally speaking, draining is most commonly used to separate any excess non-impregnated solution from the impregnated support.

Following any of the above described separation methods, the impregnated support can be subjected to a removal method to selectively and physically remove at least a portion of the impregnated solution from certain support pores of the impregnated support, the removal method preferably comprising centrifugation. In one embodiment of the present invention, following the separation of non-impregnated solution from the catalyst support, the silver-containing impregnation solution that has been impregnated and disposed in the pores of the support is selectively removed from certain pores of the support by subjecting the impregnated support to a removal means such as centrifugation.

When centrifugation is used as the removal means in the present invention, the centrifugation conditions may be chosen to selectively remove impregnated solution not only from the surface of the overall catalyst, but also from certain pores of the catalyst support. The centrifugation step is important because it separates the excess non-impregnated impregnation solution from the surface of the catalyst support that was not removed in the draining step and the impregnated solution from certain pores of the catalyst support. And, the removal of Ag impregnation solution from large pores by centrifugation eliminates the agglomeration of Ag on the surfaces of the large pores and reduces the overall average particle size of silver.

Generally, the important factors to consider for carrying out the centrifugation step of the present invention may include, for example, the speed of rotation (r.p.m.), radius of centrifuge, time, and temperature of centrifugation. The speed of rotation and the radius of the centrifuge determine the relative centrifugal force (RCF). RCF may be calculated using the following equation Eq. (1):

$$RCF = 1.12 R_c \cdot \left(\frac{r \cdot p \cdot m}{1000}\right)^2 \qquad \text{Eq. (1)}$$

wherein $R_c$ is the radius of the centrifuge (mm) and r.p.m. is the rotational speed in revolutions per minute.

The centrifugal force can be calculated from the following equation:

$$F_c = m\overline{\omega}^2 R_c = h\pi r^2 \rho \overline{\omega}^2 R_c \qquad \text{Eq. (2)}$$

wherein m is the mass of liquid present within the pores, w is the angular speed, r is the radius of the pore, h is the height of the liquid present in the pore, $R_c$ is the radius of the centrifuge, ρ is the density of the liquid. The height of the liquid inside the pore is determined by the balance between the surface tension force and the gravitational forces:

$$h = \frac{2\gamma \cos\theta}{r \rho g} \qquad \text{Eq. (3)}$$

wherein θ is the contact angle.

To selectively remove the solution from determined pores, the centrifugal force should be equal to the capillary force for the correspondent pore. The capillary force is calculated by the following equation:

$$F_{capillary} = h\gamma \cos\theta \qquad \text{Eq. (4)}$$

As a summary the optimal RCF to remove the solution located inside a certain size of pores is determined by matching the capillary with the centrifugal force. Based on this the following relationship is obtained:

$$RCF = 0.1 \left(\frac{\gamma \cos\theta}{\pi r^2 \rho}\right) \qquad \text{Eq. (5)}$$

The physical properties expressed in Eq. (5) are temperature dependent and therefore may affect the efficiency of the centrifugation process.

To further illustrate the present invention employing equation (5) above, the following properties can be used in the equation: For the properties of impregnation liquid, $\gamma = 7.28 \times 10^{-2}$ N/m; $\theta = 85°$; and $\rho = 1493$ kg m$^{-3}$ and assuming that the size of pore ranges from 1,000 μm to 1 μm, the centrifugal force (RCF) can be for example from about 0.1 to 1,500,000.

The centrifugation time can be for example from about 1 minute (min) to about 20 min in one embodiment, and from about 5 min to about 10 min in another embodiment. The temperature at which the centrifugation is performed can be a factor since it may determine the properties of the impregnation solution inside the pores. The centrifugation can be carried out at any suitable temperature; for example, not so high that the solution decomposes in the centrifuge, or at a temperature not so low that the fluid is not flowable, i.e., the solution should remain sufficiently fluid and have the necessary rheology to be removable from the support by the centrifuge. In one general embodiment, for example, the centrifugation temperature can be from about 20° C. to about 80° C. Typically, the temperature of centrifugation is at ambient temperature. In one embodiment for example, a silver amine oxalate solution of the type described herein in the Examples can be centrifuged at a temperature of from about room temperature (RT) to about 40° C.

The centrifugation step of the present invention, and/or any of the steps thereof, may be a batch process; and the equipment used in the process may be any centrifuge and ancillary equipment well known to those skilled in the art.

The centrifugation step of the present invention process is important because centrifugation separates the excess non-impregnated impregnation solution from the surface of the catalyst support and also at least a portion of the impregnated solution from pores of a particular size range in the catalyst support. In this way, the centrifugation step in conjunction with adjustment of the impregnation solution enables control of the particle size of the Ag for each type of pore in the support by tuning the concentration of Ag in the pore to match the available surface area within the pore. By selecting the centrifugation speed to provide the proper centrifugal force and centrifugation time, it is possible to control which pore modes remain filled with the Ag impregnation solution and therefore control the final Ag particle size and the location of the Ag particles within the support.

An added benefit of the centrifugation step or steps is that centrifugation can reduce the amount of non-impregnated Ag solution left on the exterior surfaces of the support pellet and reduce or even prevent the formation of a Ag crust on the pellet surface following calcination. It is hypothesized that the excess silver on the exterior chips off the catalyst during the operation leading to an accumulation of fines and an increase in pressure drop. In addition, removing excess Ag solution prior to calcination allows the solution to be recovered and enables better Ag utilization in the catalyst production process, reducing production costs.

An additional advantage to producing catalysts in this manner is that it may have overall lower silver-loading relative to current state-of-the-art catalyst without a loss of productivity. It will be appreciated that this lower silver-loading can reduce the cost of producing such catalyst. In addition, lower Ag loading and a reduction of exterior pellet deposition of Ag may: (1) cause less pore blockage and therefor reduce diffusional barriers in the catalyst, and (3) reduce subsequent loss of Ag during further catalyst handling.

Following the centrifugation step above, the resulting centrifuged support is generally heat treated, i.e., roasted, at elevated temperatures to evaporate the liquid within the support; and to effect decomposition and reduction of the silver metal salt to metallic silver, thereby effecting deposition of the silver and promoters, if present, onto the interior and exterior support surfaces.

Various heat treatment atmospheres can be employed for heating the impregnated/centrifuged supports. For example, the support may be heated in air or in an inert atmosphere such as a nitrogen atmosphere. When the heat treatment is done in an oxidative environment, the heat treatment may be referred to as "calcination".

Generally, the impregnated support is heat treated at atmospheric or sub-atmospheric pressure to remove the solvent (or solvents) present and deposit (with or without decomposition) the promoter species, if present, on to the silver and support surfaces. The heat treatment may be carried out at a temperature and for a period of time sufficient to remove the excess solvent and to convert substantially all of the silver salt to silver metal. For example, the impregnated/centrifuged support can be heated at a temperature of from about 100° C. to about 900° C. in one embodiment, and from about 200° C. to about 700° C. in another embodiment, for a period of time sufficient to convert substantially all of the silver salt to silver metal. For example, the roasting step may be carried out for a period of time from about 2 min to about 12 hours (hr).

In general, the higher the temperature, the shorter the required reduction period. For example, at a temperature of from about 400° C. to about 900° C., reduction may be accomplished in about 1 min to about 5 min. Other periods of time to thermally treat an impregnated support have been suggested in the art. For example, U.S. Pat. No. 3,563,914 suggests heating an impregnated support for less than 300 seconds to dry, but not to roast to reduce the catalyst; U.S. Pat. No. 3,702,259 discloses heating an impregnated support from 2 hr to 8 hr at a temperature of from 100° C. to 375° C. to reduce the silver salt in the catalyst; and U.S. Pat. No. 3,962,136 suggests 4 hr to 8 hr at a temperature of from 100° C. to 375° C.; all the above patents are incorporated herein by reference. Although a wide range of heating periods can be employed in the present invention, it is important that the reduction time be correlated with temperature such that substantially complete reduction of the silver salt to metal is accomplished. A continuous or step-wise heating program is desirably used for this purpose. Continuous roasting of the catalyst for a short period of time, such as for not longer than 4 hr is preferred and can be effectively done in making the catalysts of this invention. When more than one roasting step is used, it is not necessary that the roasting conditions be the same in each roasting step.

The roasting or calcination step of the present invention, and/or any of the other steps thereof, may be a batch or a continuous process. The step of the present invention process including heating the impregnated multimodal support can be carried out using any conventional heating means. For example, the equipment used for such heat treatment may include a static or flowing atmosphere of the gases to effect reduction.

A highly efficient silver-containing epoxidation catalyst useful for the selective oxidation of ethylene to ethylene oxide results from the preparation process described above. The catalyst comprises at least one catalytic species deposited on a porous support; wherein the at least one catalytic species is silver; and wherein the silver deposited on the support has a controlled average particle size in the finished catalyst.

The active components of the highly efficient catalyst produced by the process of the present invention may include Ag as the catalytic species, rhenium as a promoter, optionally, a rhenium co-promoter, and optionally other metals.

After being roasted in the heating zone, the silver impregnated catalyst can be weighed; and based upon the weight gain relative to the material prior to impregnation; the weight of silver (weight % silver) on the support can be calculated, assuming complete removal of solvent and precursor materials.

When the desired catalytic species comprises silver, generally, the wt % silver concentration supported on the support may be dependent upon silver concentration in the impregnation solution, the pore volume of the support, and number of impregnation steps used. Generally, the impregnations will desirably be sufficient to allow the appropriate amount of silver to be provided on the support. For example, the amount of silver supported on the support may be an amount greater than about 5 wt % in one embodiment, greater than about 10 wt % in another embodiment, greater than about 15 wt % in still another embodiment, greater than about 20 wt % in yet another embodiment, greater than about 25 wt % in even still another embodiment, greater than about 27 wt % in even yet another embodiment, and greater than about 30 wt % in even still another embodiment, based on the weight of the catalyst. The amount of silver provided in connection with the supports may usually be less than about 70 wt % in one embodiment, and less than about 50 wt % in another embodiment, based on the weight of the catalyst. See for example, US 2014/0371470 A1 incorporated herein by reference.

In other embodiments, the wt % silver on the support can be for example from about 5 wt % to about 70 wt % in one embodiment, from about 5 wt % to about 50 wt % in another embodiment, from about 15 wt % to about 40 wt % in still another embodiment, and from about 15 wt % to about 35 wt % in yet another embodiment.

The resulting catalyst prepared by the process of the present invention has Ag particles in desired sizes in both small and big pores of the support, sufficient to provide an improved overall catalyst performance Although silver particle size in the finished catalyst is important, the silver particle size may include a broad range. For example, a suitable silver particle size can be in the range of from about 10 angstroms to about 10,000 angstroms in diameter. Typically, the silver particle size may range from greater than about 100 angstroms to less than about 5,000 angstroms in diameter in one embodiment. It is desirable that the silver and any promoters, if employed, be relatively uniformly dispersed within, throughout, and/or on the alumina support. By the process of this invention, the silver particles have a relatively uniform particle size throughout the support as well, i.e. a relatively narrow particle size distribution.

The particle size of Ag metal deposited upon the support is a function of the catalyst preparation procedure employed. Thus, the particular choice of solvent and/or complexing agent, Ag salt, heat treatment conditions and catalyst support may affect, to varying degrees, the size of the resulting Ag particles. What is important is that the present invention provides an additional means to optimize the Ag particle size when the support has a multimodal pore size distribution.

With the process of the present invention, a Ag catalyst containing a homogeneous or uniform particle size of Ag in the catalyst can be prepared on a multimodal support. The centrifuged supported Ag catalysts of the present invention decreased the average particle size of silver when compared to Ag catalysts that were prepared on multimodal supports without a centrifugation step and/or not having homogeneous uniform particle size of Ag in the catalyst.

Generally, the catalyst prepared by the process of the present invention includes a particle size distribution of Ag in the catalyst in the range of from about 60 to about 300 nm in one embodiment, from about 60 to about 220 nm in another embodiment, and from about 90 to about 200 nm in still another embodiment. As a consequence of using a centrifugation step, the formation of Ag particles above a certain size, for example above 300 nm can be eliminated.

Catalysts according to the present invention may optionally include one or more promoters or co-promoters. For example, known promoters for silver-based, epoxidation catalysts, in addition to rhenium, may include, but are not limited to, molybdenum, tungsten, sulfur, lithium, sodium, manganese, rubidium, and cesium. Rhenium, molybdenum or tungsten may suitably be provided as oxyanions, for example, as perrhenate, molybdate, or tungstate, in salt or acid form. Examples of promoters, their characteristics, and methods for incorporating the promoters as part of the catalyst are described in U.S. Pat. No. 5,187,140, particularly at columns 11 through 15; U.S. Pat. Nos. 6,511,938; 5,504,053; 5,102,848; 4,916,243; 4,908,343; 5,059,481;

4,761,394, 4,766,105, 4,808,738, 4,820,675; and 4,833,261; all patents which are incorporated herein by reference.

The promoters and/or co-promoters, when used, may vary in concentration for example from about 0 wt % to about 1.0 wt % in one embodiment, from about 0.0005 wt % to about 1.0 wt % in another embodiment, and from about 0.005 wt % to about 0.5 wt % in still another embodiment.

In general, the present invention process can be used for oxidizing an olefin compound to an oxide product. One example of an end use where the catalyst of the present invention is advantageously used can be epoxidizing ethylene to ethylene oxide. The performance of the catalyst in such an epoxidation reaction is typically evaluated on the basis of the catalyst's selectivity, activity, and stability during the epoxidation reaction. "Stability" typically refers to how the selectivity and/or activity changes during the time that a particular batch of catalyst is being used, i.e., as more ethylene oxide is cumulatively produced. Catalysts of the present invention are expected to provide advantages in selectivity, activity and/or stability resulting from the Ag catalytic species loading and the homogeneous uniform particle size of Ag in the catalyst that can be achieved on a multimodal support material. Another advantage that may also be gained by using the process of the present invention and producing the catalyst by the process of the present invention is that production and/or equipment cost associated with the process may be decreased.

For example, after the silver-based supported catalyst is prepared as described above, the catalyst may be used in a process for epoxidizing ethylene to form an ethylene oxide, as disclosed in US 2014/0323295 A1, incorporated herein by reference. The reaction process of an epoxidation of ethylene is also described, for example, in U.S. Pat. Nos. 6,511,938 and 5,057,481; and Kirk-Othmer Encyclopedia of Chemical Technology, 4$^{th}$ Ed. (1994) Volume 9, pages 915-959; herein incorporated by reference.

Typically, epoxidation reactions may desirably be carried out in the gas phase, with a feed comprising ethylene and oxygen being caused to come in contact with the epoxidation catalyst of the present invention. Generally, the catalyst is present as a solid material, and more particularly, may be present as a packed bed within a desired reactor. The quantity of catalyst used may be any suitable amount and will depend upon the application. In one embodiment, the conversion of ethylene to ethylene oxide can be carried out, for example, in a continuous process by continuously introducing a feed stream containing ethylene and oxygen or an oxygen-containing gas to a catalyst-containing reactor. The resulting ethylene oxide is separated and recovered from the reaction products using conventional methods.

The reactor used for the conversion of ethylene to ethylene oxide using the catalysts described herein may be of a variety of reactor types, including, fixed bed tubular reactors, continuous stirred tank reactors (CSTR), and fluid bed reactors, a wide variety of which are well known to those skilled in the art and need not be described in detail herein.

Oxygen may be supplied to the reaction in an oxygen-containing stream, such as, air or as commercial oxygen, or as oxygen-enriched air. The concentration of oxygen in the reactor feed stream may vary over a wide range, and in practice, flammability is generally the limiting factor for oxygen concentration. Generally, the oxygen concentration in the reactor feed will be at least one (1) mole percent, preferably at least two (2) mole percent, and still more preferably at least four (4) mole percent. The oxygen concentration will generally be no more than fifteen (15) mole percent, preferably no more than twelve (12) mole percent, and even more preferably no more than nine (9) mole percent.

The concentration of ethylene in the reactor feed stream may vary over a wide range. However, it is preferably at least eighteen (18) mole percent and more preferably at least twenty (20) mole percent. The concentration of ethylene in the reactor feed stream is preferably no greater than 50 mole percent, and more preferably is no greater than 40 mole percent.

Generally, the epoxidation reaction is carried out at a temperature of from about 180° C. to about 315° C., and at a reactor pressure in the range of from about atmospheric to about 35 bar. The gas hourly space velocity (GHSV) may be greater than about 3,000 h$^{-1}$. The residence times in the large-scale catalyst-containing reactors are generally on the order of from about 0.5 seconds to about 2.5 seconds. The above epoxidation process conditions are generally employed depending upon the mass velocity and productivity desired.

EXAMPLES

The following examples further illustrate the present invention in more detail but are not to be construed to limit the scope thereof.

Example 1 and Comparative Example A

In these examples, the influence of centrifugation on average particle size of Ag over a support material is illustrated. Two non-promoted silver-based supported catalysts: (Catalyst 1 [Comparative Example A] and Catalyst 2 [Example 1]), are synthesized on a bimodal alpha alumina containing support produced by Saint-Gobain NorPro (herein "Support A"). The properties of Support A are described in Table I.

TABLE I

| Textural Properties of Support A | |
| --- | --- |
| Surface Area, m$^2$ g$^{-1}$ | 0.84 |
| Total Pore Volume, cm$^3$ g$^{-1}$ | 0.55 |
| Mean pore diameter, µm | 1 µm/40 µm |

Catalyst 1 (Comparative Example A) is synthesized using a conventional synthesis approach according to the following general steps:

(1) placing pellets in impregnation cylindrical vessel and applying vacuum at 29 in Hg for 15 min using a mechanical pump;

(2) vacuum impregnating the pellets from step (1) employing an oxalate/amine mixture solution at a standard concentration of 25-30 wt % Ag to form an impregnated catalyst support; the ratio of volume of carrier/volume of solution being 2/3; and the impregnation solution containing oxalic acid (16 wt %), ethylene diamine (16.3 wt %), monoethanol amine (6 wt %) and silver oxide (25-30 wt %);

(3) draining the excess impregnation solution by opening the valve on bottom of impregnation vessel to allow solution to drain for 15 min; and (4) roasting the impregnated and drained pellets from step (3) at 500° C. on a roasting belt for 2.5-3 min to form a catalyst, with an air flow of 125 standard cubic feet per hour, scfh.

Catalyst 2 (Example 1) is synthesized using the same procedure used to prepare Catalyst 1 as described above, except that after the draining step (3) and before the roasting step (4), a centrifugation step is performed. The centrifugation step is carried out at 1,000 rotations per minute (rpm) for 5 min using a centrifuge with a Sorvall SH-3000 rotor having a radius of 182 millimeters (mm) (RCF~204). To ensure that the excess Ag impregnation solution is kept separate from the catalyst pellets, the container in which the impregnated support is centrifuged contains a porous or absorbent material at the bottom.

This support with a pore volume of 0.55 $cm^3/g$ retains 0.57 $cm^3/g$ of impregnation solution of which ~0.24 $cm^3/g$ is removed by the centrifugation step.

Scanning electron microscopy (SEM) fracture cross section images representative of catalysts prepared on a multimodal support with and without inclusion of a centrifugation step are presented in FIGS. 5a and 5b. For example, FIG. 5a shows a SEM micrograph of the larger pore mode of the catalyst of Comparative Example A (non-centrifuged) while FIG. 5b shows the same feature of the catalyst of Example 1 (centrifuged).

The Ag contents for the non-centrifuged Ag impregnated support material (Comparative Example A) and the centrifuged Ag impregnated support material (Example 1) are 17.5 wt %, and 11.2 wt %, respectively. The lower percentage of Ag on the centrifuged sample (Catalyst 2) is consistent with the selective removal of Ag impregnation solution from the large pores and the pellet external solution film, in which the capillary forces are weaker than centrifugation induced forces.

The Ag morphology and particle size for Catalyst 1 and Catalyst 2 are evaluated by SEM and are shown in FIGS. 5a and 5b, respectively. The removal of Ag impregnation solution from large pores by centrifugation eliminates the agglomeration of Ag on the surfaces of the large pores and reduced the overall average particle size of silver.

Example 2 and Comparative Example B

In this example, the influence of centrifugation on the average particle size of Ag on a multimodal support is illustrated. Two non-promoted silver-based supported catalysts: (Catalyst 3 [Comparative Example B.] and Catalyst 4 [Example 2]), are synthesized on Support B. Support B is a bimodal alpha alumina containing support produced by Saint-Gobain NorPro. The properties of Support B are described in Table II.

TABLE II

| Textural Properties of Support B | |
|---|---|
| Surface Area, $m^2\ g^{-1}$ | 0.88 |
| Total Pore Volume $V_p$, $cm^3\ g^{-1}$ | 0.52 |
| Mean pore diameter, μm | 1 μm/40 μm |

Catalyst 3 is synthesized using a conventional synthesis approach according to the following general steps:

(1) placing support pellets in impregnation cylindrical vessel and applying vacuum at 29 in Hg for 15 min using a mechanical pump;

(2) vacuum impregnating the pellets from step (1) employing an oxalate/amine mixture solution at a standard concentration of 25-30 wt % Ag to form an impregnated catalyst support; the ratio of volume of carrier/volume of solution being 2/3; and the impregnation solution containing oxalic acid (16 wt %), ethylene diamine (16.3 wt %), monoethanol amine (6 wt %) and silver oxide (25-30 wt %);

(3) draining the excess impregnation solution by opening the valve on bottom of impregnation vessel to allow solution to drain for 15 min; and (4) roasting the impregnated and drained pellets from step (3) at 500° C. on a roasting belt for 2.5-3 min to form a catalyst, with an air flow of 125 scfh.

Catalyst 4 is synthesized using the same procedure as for Catalyst 3, except that a centrifugation step is performed after the first impregnation step (2). Centrifugation is carried out using a Sorvall ST-16 centrifuge. The rotor inside the centrifuge is rated for 5,000 rpm and the rotor has a radius of 16.2 cm. The centrifugation is carried out at 5,000 rpm for 8 min (RCF~4,536). To ensure that the excess Ag impregnation solution is kept separate from the catalyst pellets, the container in which the impregnated support is centrifuged contains a porous or absorbent material at the bottom.

The dispersion of Ag on Catalyst 3 and 4 is evaluated by CO pulse chemisorption and SEM.

Prior to CO chemisorption, Catalyst 3 (Comparative Example B) and Catalyst 4 (Example 2) are subjected to an outgassing step at 170° C. for 1 hr followed by a pretreatment in 10 volume percent (vol %) $O_2$/He at 170° C. for 1 hr to create a sub-surface oxygen layer on the silver particles. Subsequently, the subsurface oxygen is titrated by pulsing with CO at 170° C. until $CO_2$ formation is no longer detected. Every $CO/CO_2$ pulse is quantified using a mass spectrometer positioned downstream of the reactor.

SEM fracture cross section images of Catalysts 3 and 4 are presented in FIGS. 6a and 6b. As can be observed from FIGS. 6a and 6b, the centrifugation step eliminates the formation of large aggregates of Ag around the large pore areas.

Figure 7A:
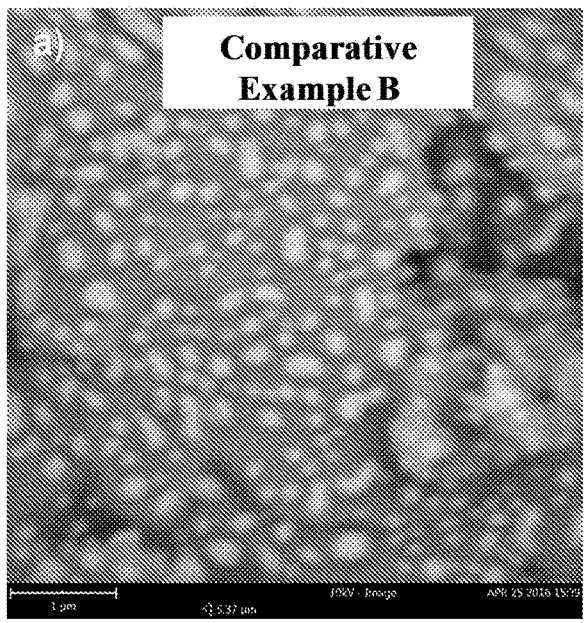
FIG. 7a is a SEM fracture cross section image of Ag particles in the smaller diameter pore mode of a multimodal EO catalyst support, where the Ag impregnation is performed by a single impregnation step (conventional synthesis without a centrifugation step).
Figure 7B:
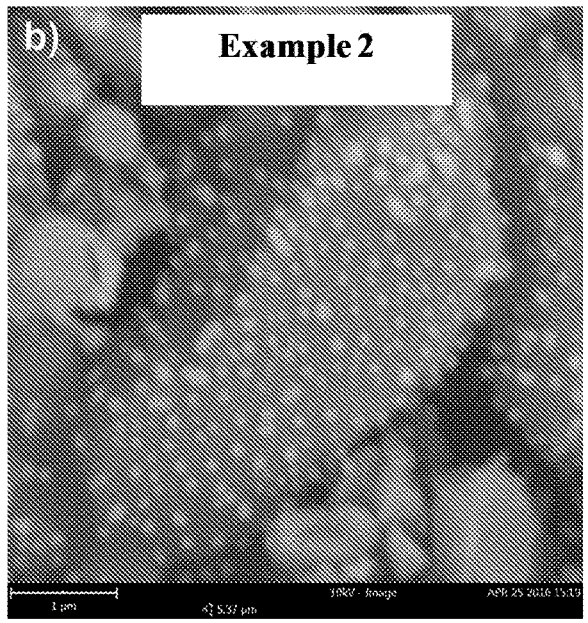
FIG. 7b is a SEM fracture cross section image of Ag particles found in the smaller diameter pore mode of a multimodal EO catalyst support, where Ag is impregnated in a single step followed by a centrifugation step, as described in FIG. 2.

The mean equivalent circle diameters calculated from the distribution of at least 250 particles in small pore regions of Catalysts 3 and 4 are shown in FIGS. 7a and 7b, respectively and Table III. Catalyst 3 and Catalyst 4 have an average particle size ~ of 140 nm and 100 nm, respectively.

The average particle size of silver obtained for centrifuged samples by CO chemisorption measurements are very comparable with the ones obtained by microscopy, with both techniques demonstrating that the centrifugation reduces Ag particle size (leading to higher Ag surface areas for a given weight of applied Ag, and more efficient use of Ag). These results are summarized in Table III. The Ag contents for the non-centrifuged Ag impregnated support material and the centrifuged Ag impregnated support material are 17.4 wt %, and 10.2 wt %, respectively.

TABLE III

| Ag Loading and Average Ag Particle Size for Catalysts. | | | | | |
|---|---|---|---|---|---|
| Example No. | FIG. No. | Catalyst No. | Ag (wt %) | $<D>_{SEM}$ (nm) | $<D>_{CO}$ (nm) |
| Comparative Example B | FIGS. 6a, 7a | Catalyst 3 | 17.4 | 140 ± 50 | 200 |
| Example 2 | FIGS 6b, 7b | Catalyst 4 | 10.1 | 100 ± 30 | 118 |

Example 3 and Comparative Example C

In this example, the influence of centrifugation on the average particle size of Ag on a multimodal support is illustrated. Two non-promoted silver-based supported catalysts Catalyst 5 (Comparative example C) and Catalyst 6 (Example 3) are synthesized on Support B.

Catalyst 5 (Comparative Example C) is synthesized using a conventional synthesis according to the following general steps:

(1) placing support pellets in impregnation cylindrical vessel and apply vacuum at 29 in Hg for 15 min using a mechanical pump;

(2) vacuum impregnating the pellets from step (1) employing an oxalate/amine mixture solution at a standard concentration of 25-30 wt % Ag to form an impregnated catalyst support; the ratio of volume of carrier/volume of solution being 2/3; and the impregnation solution containing oxalic acid (16 wt %), ethylene diamine (16.3 wt %), monoethanol amine (6 wt %) and silver oxide (25-30 wt %);

(3) draining the excess impregnation solution by opening the valve on bottom of impregnation vessel to allow solution to drain for 15 min;

(4) roasting the impregnated and drained pellets from step (3) at 500° C. on a roasting belt for 2.5-3 min to form a catalyst, with an air flow of 125 scfh;

(5) vacuum impregnating the calcined pellets from step (4) employing an oxalate/amine mixture solution at a standard concentration of 25 wt % Ag; the ratio of volume of carrier/volume of solution being 2/3; and the impregnation solution containing oxalic acid (16 wt %), ethylene diamine (16.3 wt %), monoethanol amine (6 wt %) and silver oxide (25-30 wt %);

(6) draining the excess impregnation solution by opening the valve on bottom of impregnation vessel to allow solution to drain for 15 min; and (7) roasting the impregnated and drained pellets from step (6) at 500° C. on a roasting belt for 2.5-3 min to form a catalyst, with an air flow of 125 scfh.

Catalyst 6 (Example 3) is synthesized using the same procedure as for Catalyst 5 as described above, except that a first centrifugation step is performed after the first impregnation step (2) and a second centrifugation step is performed after the second impregnation step (5). Each of the centrifugation steps is carried out at 5,000 rpm for 8 min (RCF~4,536).

The average particle size of Ag on Catalyst 5 and 6 is evaluated by CO pulse chemisorption and SEM.

Prior to CO chemisorption, the catalysts are subjected to an outgassing a step at 170° C. for 1 hr followed by a pre-treatment in 10 vol % $O_2$/He at 170° C. for 1 hr to create a subsurface oxygen layer on the silver particles. Subsequently, the subsurface oxygen is titrated by pulsing CO at 170° C. until $CO_2$ formation is no longer detected. Every $CO/CO_2$ pulse is quantified using a mass spectrometer positioned downstream of the reactor.

Figure 8A:
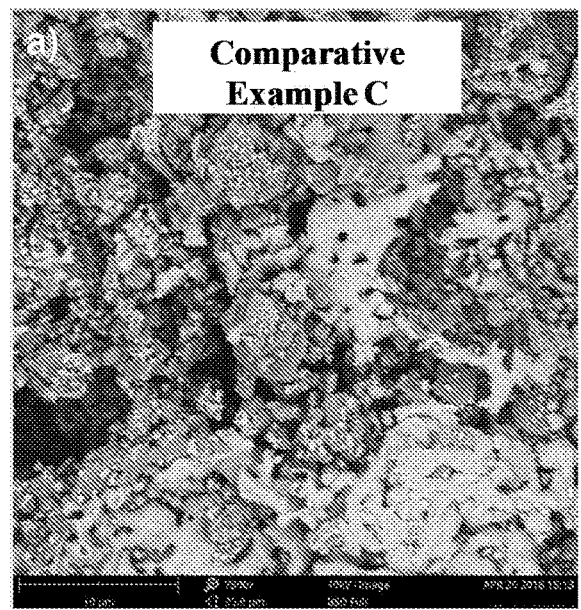
FIG. 8a is a SEM fracture cross section image of Ag particles found in the larger diameter pore mode of a multimodal EO catalyst support, where the Ag impregnation is performed in two sequential steps without centrifugation (conventional synthesis without a centrifugation step).
Figure 8B:
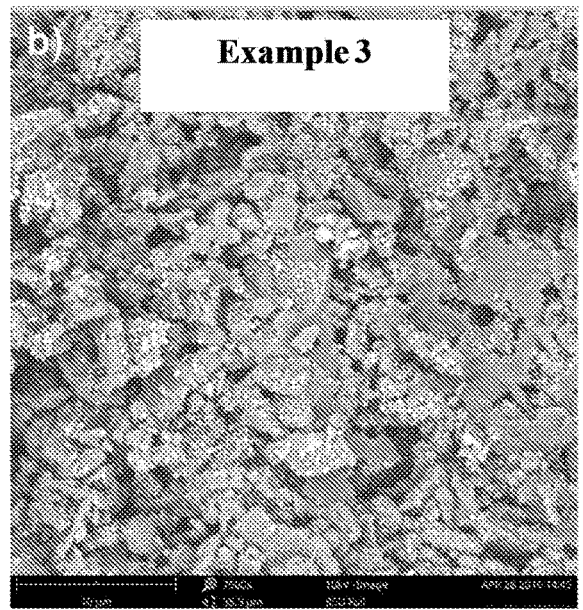
FIG. 8b is a SEM fracture cross section image of Ag particles found in the larger diameter pore mode of a multimodal EO catalyst support, where Ag is impregnated in two sequential steps each followed by a centrifugation step prior to calcination as described in FIG. 4.

SEM fracture cross section images of a larger pore mode region in Catalysts 5 and 6 are presented in FIGS. 8a and 8b. As can be observed from FIGS. 8a and 8b, the centrifugation step increases the dispersion of Ag in larger pore areas, eliminating the formation of large aggregates of Ag.

Figure 9A:
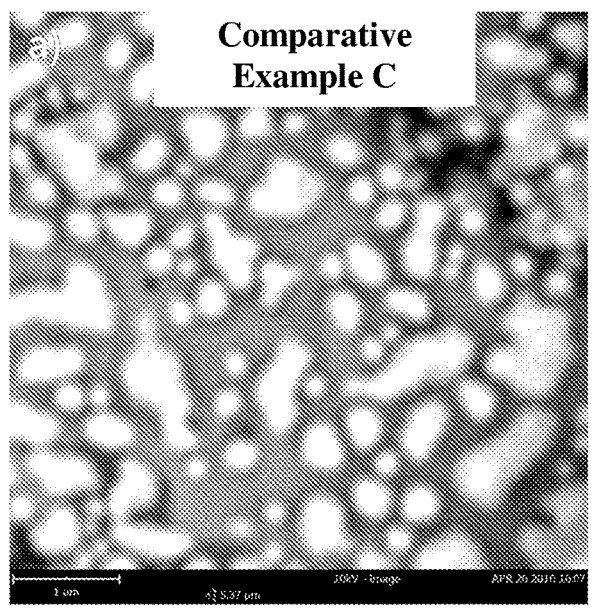
FIG. 9a is a SEM fracture cross section image of Ag particles found in the smaller diameter pore mode of a multimodal EO catalyst support, where the Ag impregnation is performed in two sequential steps without centrifugation (conventional synthesis without a centrifugation step).
Figure 9B:
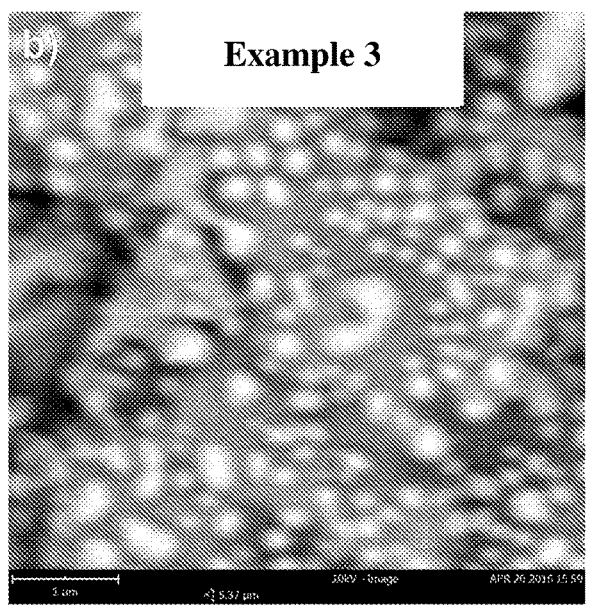
FIG. 9b is a SEM fracture cross section image of Ag particles found in the smaller diameter pore mode of a multimodal EO catalyst support, where Ag is impregnated in two sequential steps each followed by a centrifugation.

FIGS. 9a and 9b show SEM images of smaller diameter pore modes. The average particle size obtained from at least 230 particles demonstrate that the centrifuged catalyst has reduced average particle size of silver on smaller pores (244 nm vs 140 nm for catalyst 5 and 6, respectively, see Table IV).

TABLE IV

Ag Loading and Average Ag Particle Size for Catalysts

| Example No. | FIG. No. | Catalyst No. | Ag (wt %) | $<D>_{SEM}$ (nm) | $<D>_{CO}$ (nm) |
|---|---|---|---|---|---|
| Comparative Example C | FIG. 8a, 9a | Catalyst 5 | 29.35 | 244 | 232 |
| Example 3 | FIG. 8b, 9b | Catalyst 6 | 14.79 | 140 ± 50 | 130 |

Table IV summarizes the average particle size of Ag obtained for Comparative Example D and Example 4, as well as the Ag content. The Ag content for the non-centrifuged Ag impregnated support material and the centrifuged Ag impregnated support material is 29.35 wt %, and 14.79 wt %, respectively. Catalyst 5 is not very homogeneous and contains large Ag agglomerates (400 nm) as seen in FIG. 8a. Both techniques suggest that Ag particle size on Catalyst 6 (Example 4) is significantly smaller than on Catalyst 5 (Comparative Example C).

Example 4 and Comparative Example D: Catalytic Results

In this example, the influence of centrifugation on catalytic performance was evaluated. Two non-promoted silver-based supported catalysts Catalyst 3 (Comparative example B) and Catalyst 4 (Example 2) are synthesized on Carrier B.

The catalytic testing was performed in a High Pressure Reactor Assembly Module (HPRAM) II system provided by the Foundation for Scientific and Industrial Research at the Norwegian Institute of Technology. The reactor feed gas comprises ethylene (35 mol %), ethane (0.29-0.58 mol %), oxygen (7.2 mol %), $CO_2$ (1.4 mol %), ethyl chloride (1.3-5.0 ppm by volume) and methane (10 mol %), with the balance being helium. The reactor temperature is maintained at 240° C., while the reactor pressure was kept at 11 bar.

During each run, the reactor is charged with 100 mg of the catalyst (30/50 mesh) without inert diluents. The reactor is heated under helium flow, and all feed gases except oxygen are fed to it. Approximately 2-3 minutes after introducing the other feed gases to the reactor, oxygen is introduced. The target gas hourly space velocity is 10,000 $h^{-1}$ for each catalyst, which is calculated based on the actual weight of powders and the bulk packing density (0.761 g/ml) for full pellets of the catalysts. During the test a certain amount of ethyl chloride is added in the gas phase to increase the selectivity towards epoxide. The catalyst chloriding effectiveness (Z*) of the process is defined as follows:

$$Z^* = \frac{ECl}{C_2H_6 + 0.01 C_2H_4}$$

wherein ECl is the concentration in ppmv of ethyl chloride, and $C_2H_6$ and $C_2H_4$ are the concentrations in mole percent of ethane and ethylene, respectively, in the reactor feed stream.

After an activation period of 29 hours, hr, Z* is traversed through a range of values for each catalyst and the ethylene oxide concentration in the reactor outlet is measured multiple times at each Z* value. The activation period was performed at 245° C. and varying the Z* from 4 and held for 4 hr to 6.0 and held for 24 hr) and then back to 4 again and held for 4 hr. After break-in the temperature of the reaction was decreased to 240° C. and the Z* was adjusted to 4.0, 6 and 8.0, each of which is maintained for 36 hr. Reaction temperature, gas hourly space velocity, and feed gas composition are otherwise held constant during this segment of each run.

Figure 10:
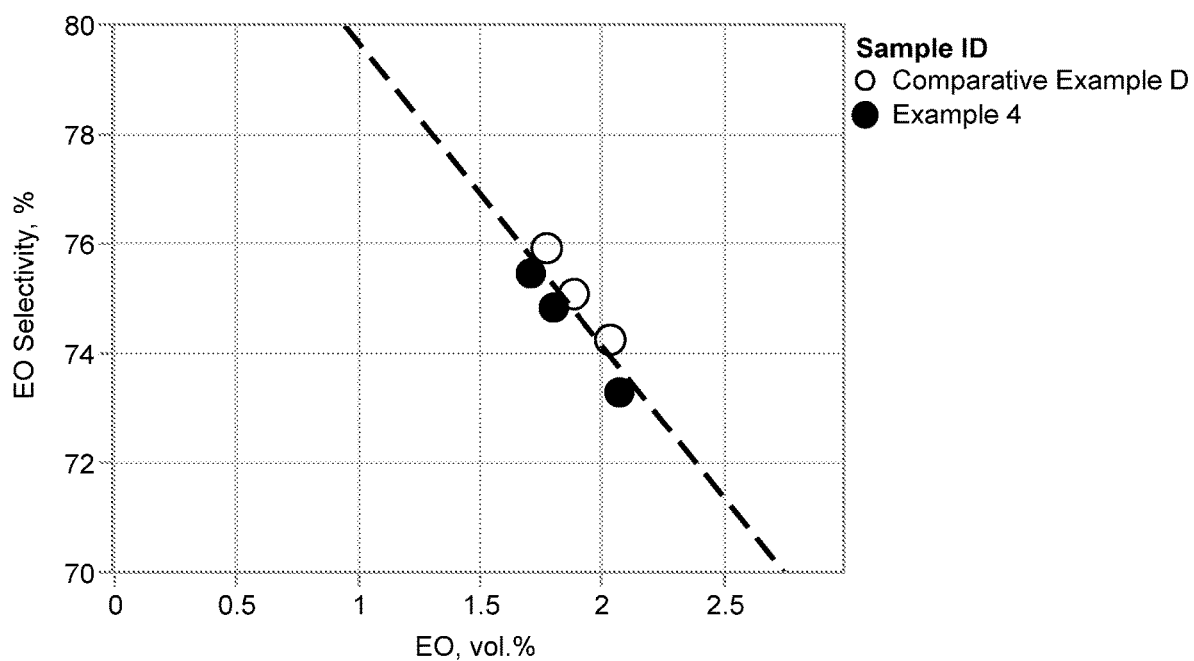
FIG. 10 compares the catalytic performance of 2 catalysts where Ag is impregnated in a multimodal carrier in 1 step with and without centrifugation prior to calcination as described in FIGS. 6a and 6b.

The catalytic performance of Catalyst 3 and Catalyst 4 are summarized in Table V for a Z* of 8.0 and FIG. 10. The catalytic activity is expressed as silver time yield (STY) and is defined as the moles of EO produced per second and per gram of silver.

As can be observed in Table V, the intrinsic activity of Ag on Catalyst 4 is 1.7 times higher in activity in comparison with Catalyst 3, demonstrating the advantage of centrifugation on improving the epoxidation performance. Furthermore, the selectivity of these catalysts is very similar.

TABLE V

Catalytic Performance of Catalyst 3 and Catalyst 4 in Epoxidation of Ethylene to Ethylene Oxide at 240° C., 11 bar, 35 vol % $C_2H4$, 7.0 vol % $O_2$ and 1.5 vol % $CO_2$

| | | | Performance at Z* = 8.0 | | |
|---|---|---|---|---|---|
| Example No. | FIG. No. | Catalyst No. | ΔEO, mol. % | $S_{EO}$, % | STY, µmol $g_{Ag}^{-1}s^{-1}$ |
| Comparative Example D | FIG. 10 | Catalyst 3 | 1.77 ± 0.1 | 76.0 ± 0.7 | 16.2 |
| Example 4 | FIG.10 | Catalyst 4 | 1.70 ± 0.1 | 75.5 ± 0.7 | 27.2 |

ΔEO—represents the outlet concentration of ethylene oxide in mol %
$S_{EO}$ represents the selectivity towards ethylene oxide (EO) and is calculated using the following expression:
$$S_{EO}(\%) = \frac{2EO(vol.\%)}{2EO(vol.\%) + CO_2(vol.\%)}$$

What is claimed is:

1. A process for preparing a silver-containing catalyst for the epoxidation of olefins comprising the steps of:
   (a) providing a porous multimodal support having at least a first set of support pores of a first size range and at least a second set of support pores of a second size range wherein the second size range of the second set of support pores is smaller than the first size range of the first set of support pores;
   (b) providing a first silver-containing impregnation solution for impregnating the first silver-containing impregnation solution into the at least first set of support pores and the at least second set of support pores of the porous multimodal support;
   (c) impregnating, one or more times, the porous multimodal support with the first silver-containing impregnation solution from step (b) to provide the porous multimodal support with a first amount of silver-containing impregnation solution; and
   (d) selectively removing at least a portion of the impregnated first silver-containing impregnation solution from the porous multimodal support to provide the porous multimodal support with a second amount of first silver-containing impregnation solution remaining in the support pores; wherein at least a portion of the impregnated first silver-containing impregnation solution is removed from the at least first set of support pores of the porous multimodal support by subjecting, one or more times, the impregnated porous multimodal support after the impregnation step (c) to a removal means for a time sufficient to selectively remove at least a portion of the impregnated first silver-containing impregnation solution contained in the at least first set of support pores of the porous multimodal support, wherein the removal means is centrifugation.

2. The process of claim 1, wherein the selectively removing step (d) removes at least 20 percent of the impregnated first silver-containing impregnation solution contained in the at least first set of support pores of the porous multimodal support.

3. The process of claim 1, including step (e) roasting, one or more times, the impregnated porous multimodal support produced in step (d) for a time and temperature sufficient to form a silver-containing catalyst useful for the epoxidation of olefins.

4. The process of claim 1, wherein the selectively removing step (d) is carried out, one or more times, by one or more centrifugation means.

5. The process of claim 1, wherein the impregnation step (c) is carried out two or more times; or wherein the removing step (d) is carried out two or more times and under two or more different process conditions.

6. The process of claim 4, wherein the impregnating step (c) is carried out two or more times prior to the removal step (d).

7. The process of claim 3, wherein the selective removal step (d) is carried out two or more times prior to the roasting step (e) or wherein the roasting step (e) is carried out two or more times.

8. The process of claim 1, wherein the first pore size range of the first set of pores of the support is from about 3 microns to about 200 microns; and wherein the second pore size range of the second set of pores of the support is from about 0.01 micron to about 3 microns, wherein pore size is determined by mercury porosimetry.

9. The process of claim 1, wherein the first silver-containing impregnation solution further comprises one or more promoters.

10. The process of claim 1, wherein the support comprises alpha-alumina.

11. The process of claim 1, wherein a silver loading of at least 10 weight percent is provided on the porous multimodal support, based on the total weight of the porous multimodal support.

12. The process of claim 3, wherein the process includes the following steps in sequence:
   (f) providing a second silver-containing impregnation solution for impregnating the second silver-containing impregnation solution into the at least first set of support pores and the at least second set of support pores of the porous multimodal support;
   (g) impregnating, one or more times, the porous multimodal support obtained in step (e) with at least a portion of the second silver-containing impregnation solution from step (f);
   (h) selectively removing, one or more times, the impregnated second silver-containing impregnation solution from the at least first set of support pores of the porous multimodal catalyst support by subjecting, at least once, the impregnated porous multimodal support after the impregnation step (g) to a removal means for a time sufficient to selectively remove a portion of the impregnated second silver-containing impregnation solution contained in the at least first set of support pores of the porous multimodal catalyst support;
   (i) roasting, one or more times, the impregnated porous multimodal support from step (h) for a time and temperature sufficient to form a silver-containing catalyst useful for the epoxidation of olefins;
   (j) providing a third silver-containing impregnation solution for impregnating the third silver-containing impregnation solution into the at least first set of support pores and the at least second set of support pores of the porous multimodal support;

(k) impregnating, one or more times, the silver-containing catalyst from step (i) with at least a portion of the third silver-containing impregnation solution from step (j);

(l) selectively removing, one or more times, the impregnated third impregnation solution from the at least first set of support pores of the impregnated roasted porous multimodal catalyst support from step (i) by subjecting, one or more times, the impregnated roasted porous multimodal support after the impregnation step (k) to a removal means for a time sufficient to selectively remove at least a portion of the impregnated third silver-containing impregnation solution contained in the at least first set of support pores of the impregnated roasted porous multimodal catalyst support; and (m) roasting, one or more times, the impregnated catalyst support member from step (l) for a time and temperature sufficient to form a silver-containing catalyst useful for the epoxidation of olefins.

\* \* \* \* \*